(12) United States Patent
Letter et al.

(10) Patent No.: US 10,274,718 B2
(45) Date of Patent: **\*Apr. 30, 2019**

(54) SINGLE-AXIS INSPECTION SCOPE WITH ANTI-ROTATION EXTENSION AND METHOD FOR INTERNAL INSPECTION OF POWER GENERATION MACHINERY

(71) Applicant: Siemens Energy, Inc., Orlando, FL (US)

(72) Inventors: David Letter, Deland, FL (US); Isaac Piersall, Winter Springs, FL (US); Clifford Hatcher, Jr., Orlando, FL (US)

(73) Assignee: SIEMENS ENERGY, INC., Orlando, FL (US)

( \* ) Notice: Subject to any disclaimer, the term of this patent is extended or adjusted under 35 U.S.C. 154(b) by 140 days.

This patent is subject to a terminal disclaimer.

(21) Appl. No.: 15/493,211

(22) Filed: Apr. 21, 2017

(65) Prior Publication Data
US 2017/0219814 A1     Aug. 3, 2017

Related U.S. Application Data

(63) Continuation-in-part of application No. 15/212,370, filed on Jul. 18, 2016, now Pat. No. 9,948,835, which
(Continued)

(51) Int. Cl.
    *G01M 15/14*     (2006.01)
    *G02B 23/24*     (2006.01)
    (Continued)

(52) U.S. Cl.
    CPC ....... *G02B 23/2476* (2013.01); *F01D 21/003* (2013.01); *G01M 15/02* (2013.01);
(Continued)

(58) Field of Classification Search
    USPC .............................. 73/112.01, 112.02, 112.05
See application file for complete search history.

(56) References Cited

U.S. PATENT DOCUMENTS

| 4,216,802 A | 8/1980 | Bonnes et al. |
| 5,102,221 A | 4/1992 | Desgranges et al. |

(Continued)

FOREIGN PATENT DOCUMENTS

EP     0907077 A2     4/1999

OTHER PUBLICATIONS

Utility U.S. Appl. No. 13/971,938, filed Aug. 21, 2013, now U.S. Pat. No. 9,154,743 issued on Oct. 6, 2015.
(Continued)

*Primary Examiner* — Eric S. McCall

(57) ABSTRACT

Internal components of power generation machinery, such as gas turbine engines, are inspected with a spherical, optical-camera inspection system, mounted within a camera housing on a distal end of a compact diameter, single-axis inspection scope. The inspection scope includes nested, non-rotatable telescoping tubes, which define an extension axis. Circumscribing, telescoping tubes have anti-rotation collars, which are in sliding engagement with extension tracks on a circumferential surface of an opposing, nested tube, for ease of extension and retraction of the camera during visual inspections of power generation machinery. The camera is advanced and/or retracted along a scope extension axis by nested, drive tubes, which incorporate at least one external drive screw on a circumscribed drive tube and corresponding female threads formed in a circumscribing drive tube. The spherical camera has a 360-degree field of view, and captures images without rotation about the scope extension axis.

20 Claims, 10 Drawing Sheets

Related U.S. Application Data is a continuation-in-part of application No. 14/803,149, filed on Jul. 20, 2015, now Pat. No. 9,778,141, which is a continuation-in-part of application No. 13/362,352, filed on Jan. 31, 2012, now Pat. No. 8,713,999.

(60) Provisional application No. 61/692,393, filed on Aug. 23, 2012, provisional application No. 61/692,409, filed on Aug. 23, 2012.

(51) Int. Cl.
| | |
|---|---|
| *G01M 15/02* | (2006.01) |
| *G01N 21/954* | (2006.01) |
| *H04N 5/225* | (2006.01) |
| *H04N 5/232* | (2006.01) |
| *F01D 21/00* | (2006.01) |
| *G02B 13/06* | (2006.01) |

(52) U.S. Cl.
CPC .......... *G01M 15/14* (2013.01); *G01N 21/954* (2013.01); *G02B 13/06* (2013.01); *G02B 23/2484* (2013.01); *H04N 5/2251* (2013.01); *H04N 5/2252* (2013.01); *H04N 5/2257* (2013.01); *H04N 5/23238* (2013.01); *F05D 2260/83* (2013.01); *F05D 2270/80* (2013.01); *F05D 2270/8041* (2013.01); *G01N 2021/9544* (2013.01); *G01N 2201/062* (2013.01); *H04N 2005/2255* (2013.01)

(56) References Cited

U.S. PATENT DOCUMENTS

| | | | |
|---|---|---|---|
| 5,164,826 A | 11/1992 | Dailey | |
| 5,349,850 A | 9/1994 | Young | |
| 6,317,387 B1 | 11/2001 | D'Amaddio et al. | |
| 6,867,586 B2 * | 3/2005 | Hatcher ............... | G01N 27/902 324/239 |
| 6,992,315 B2 | 1/2006 | Twerdochlib | |
| 7,068,029 B2 | 6/2006 | Hatcher et al. | |
| 7,271,894 B2 | 9/2007 | Devitt et al. | |
| 7,489,811 B2 | 2/2009 | Brummel et al. | |
| 7,956,326 B1 | 6/2011 | Kychakoff et al. | |
| 8,184,151 B2 | 5/2012 | Zombo et al. | |
| 8,299,785 B2 | 10/2012 | Bousquet et al. | |
| 8,713,999 B2 | 5/2014 | Hatcher | |
| 8,786,848 B2 * | 7/2014 | Hatcher ............... | F01D 9/023 348/83 |
| 8,922,640 B2 | 12/2014 | Hatcher et al. | |
| 2004/0051525 A1 | 3/2004 | Hatcher et al. | |
| 2004/0193016 A1 | 9/2004 | Root et al. | |
| 2005/0199832 A1 | 9/2005 | Twerdochlib | |
| 2005/0200355 A1 | 9/2005 | Hatcher et al. | |
| 2006/0088793 A1 | 4/2006 | Brummel et al. | |
| 2007/0129604 A1 | 6/2007 | Hatcher et al. | |
| 2007/0157733 A1 | 7/2007 | Litzenberg et al. | |
| 2007/0296964 A1 | 12/2007 | Nishimura et al. | |
| 2011/0018530 A1 | 1/2011 | Bousquet et al. | |
| 2011/0267428 A1 | 11/2011 | George et al. | |
| 2012/0154594 A1 | 6/2012 | Xie et al. | |
| 2012/0281084 A1 | 11/2012 | Hatcher et al. | |
| 2013/0194412 A1 | 8/2013 | Hatcher et al. | |
| 2013/0194413 A1 | 8/2013 | Hatcher et al. | |
| 2014/0168420 A1 | 6/2014 | Naderhirn et al. | |
| 2015/0241303 A1 * | 8/2015 | DeAscanis ............ | G01M 15/02 348/82 |
| 2015/0341600 A1 * | 11/2015 | Hatcher, Jr. ............ | H04N 7/183 348/82 |
| 2016/0012576 A1 * | 1/2016 | Hatcher, Jr. ........... | F01D 21/003 348/82 |
| 2017/0219815 A1 * | 8/2017 | Letter ................ | H04N 5/23238 |

OTHER PUBLICATIONS

Utility U.S. Appl. No. 13/362,417, filed Jan. 31, 2012, now U.S. Pat. No. 9,057,710 issued on Jun. 16, 2015.
Utility U.S. Appl. No. 13/362,352, filed Jan. 31, 2012, now U.S. Pat. No. 8,713,999 issued on May 6, 2014.
Utility U.S. Appl. No. 13/362,387, filed Jan. 31, 2012, now U.S. Pat. No. 8,922,640 issued on Dec. 30, 2014.
Utility U.S. Appl. No. 13/972,000, filed Aug. 21, 2013, now U.S. Pat. No. 9,116,071 issued on Aug. 25, 2015.
Co-pending Utility U.S. Appl. No. 14/732,982, filed Jun. 8, 2015.
Co-pending Utility U.S. Appl. No. 14/803,149, filed Jul. 20, 2015.
Co-pending Utility U.S. Appl. No. 15/212,370, filed Jul. 18, 2016.

* cited by examiner

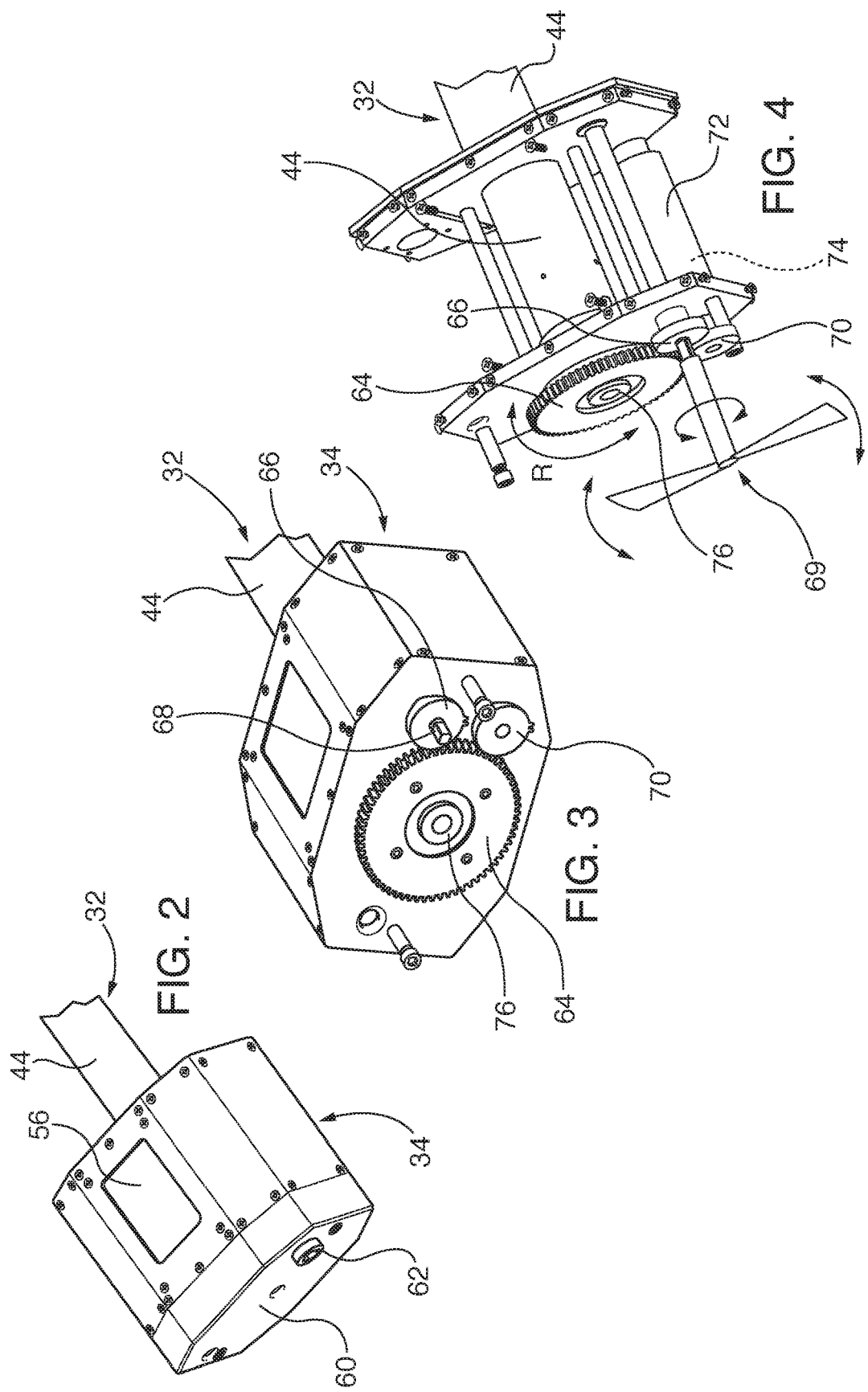

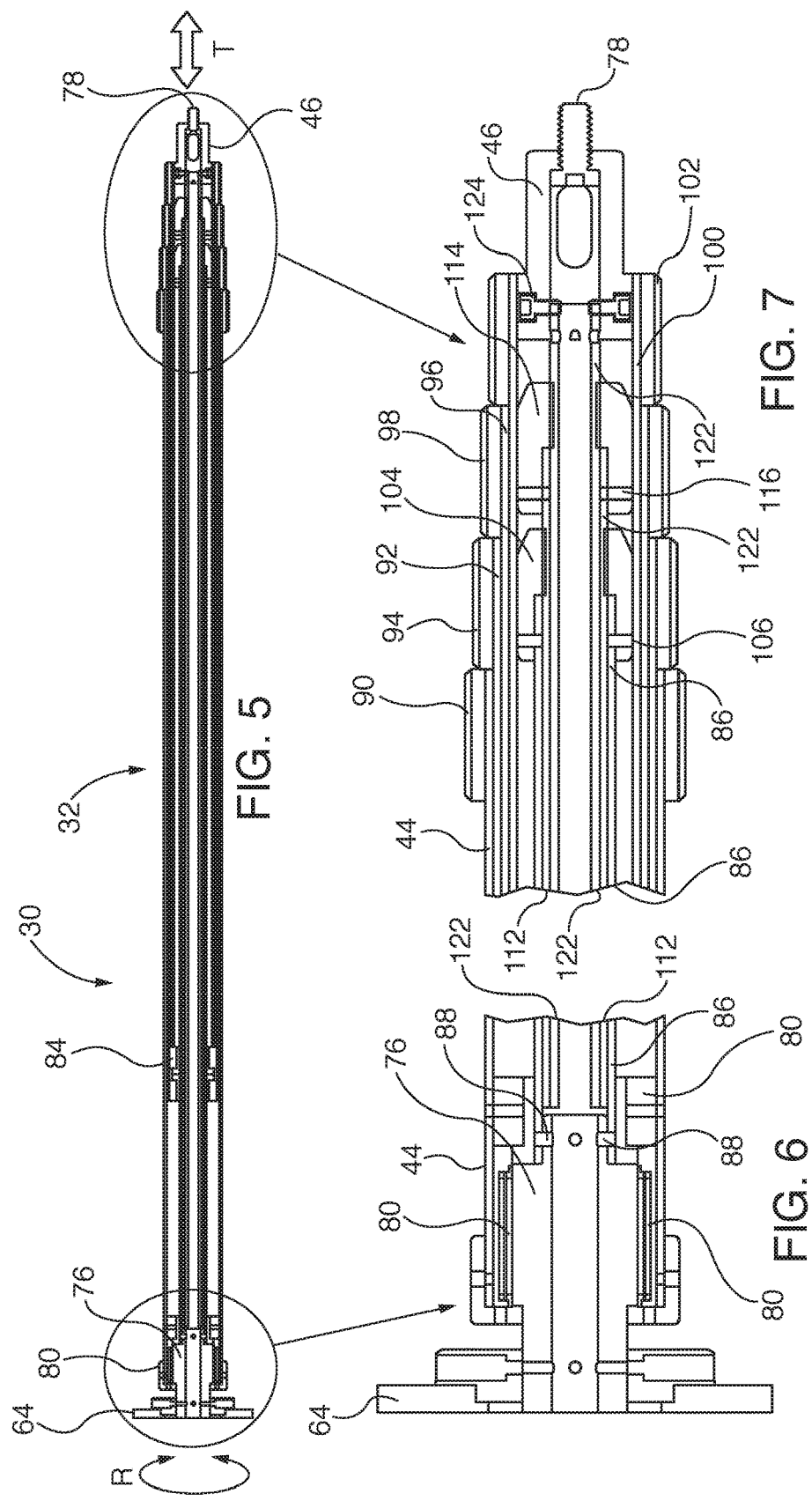

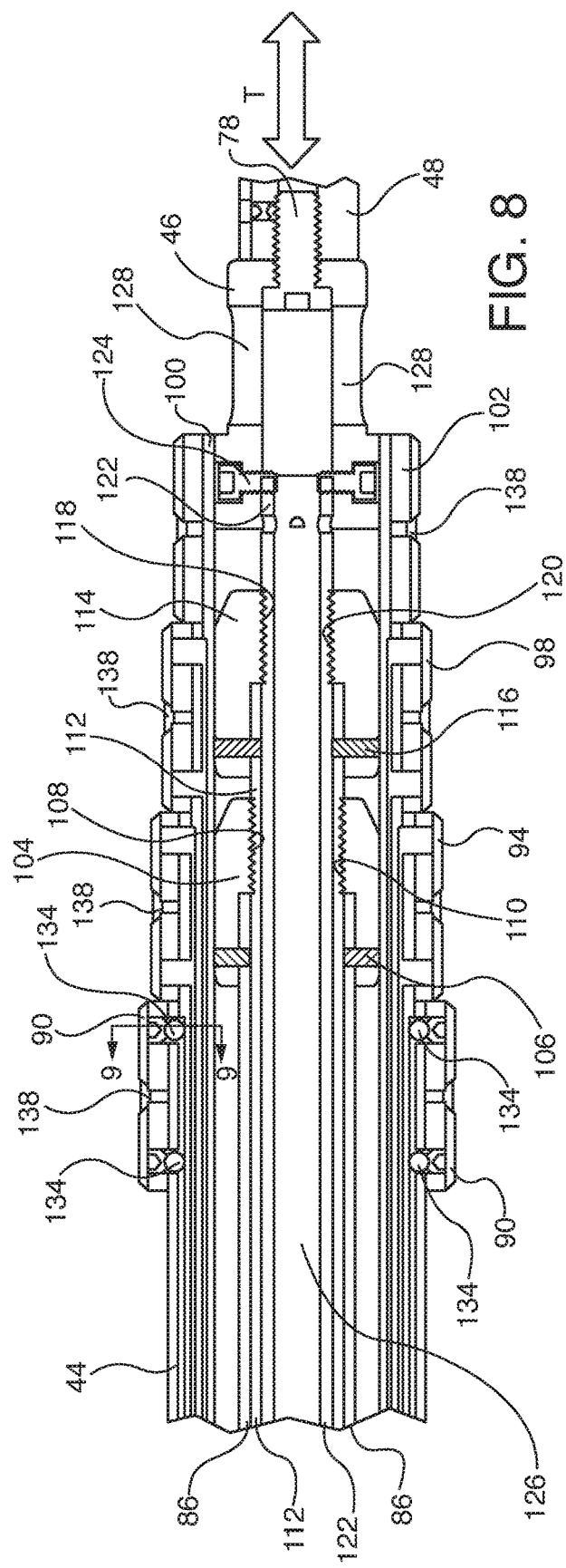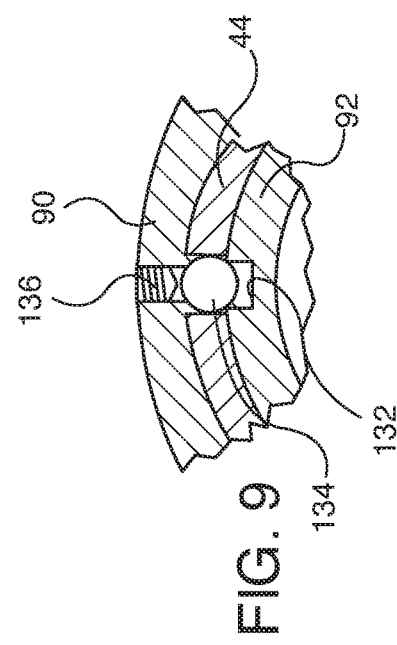

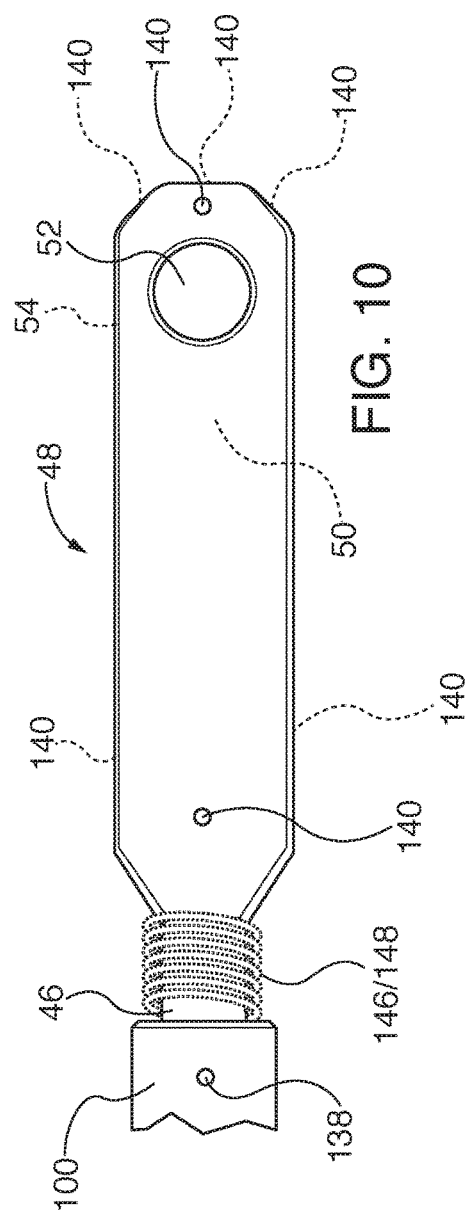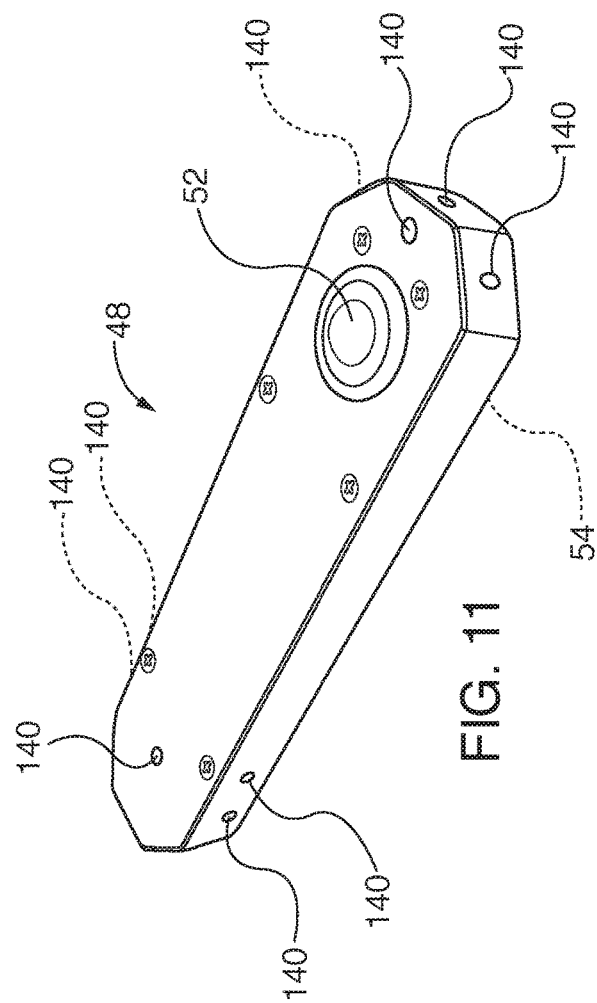

SINGLE-AXIS INSPECTION SCOPE WITH ANTI-ROTATION EXTENSION AND METHOD FOR INTERNAL INSPECTION OF POWER GENERATION MACHINERY

PRIORITY CLAIM

This application claims priority under, and is a continuation-in-part of U.S. utility patent application Ser. No. 15/212,370, filed Jul. 18, 2016, and entitled "Single-Axis Inspection Scope with Spherical Camera and Method for Internal Inspection of Power Generation Machinery", which is a continuation-in-part of U.S. utility patent application Ser. No. 14/803,149, filed Jul. 20, 2015, and entitled "Optical Inspection Scope with Deformable, Self-Supporting Deployment Tether", which is a continuation-in-part of U.S. utility patent application Ser. No. 13/362,352, filed Jan. 31, 2012, and entitled "System and Method For Automated Optical Inspection of Industrial Gas Turbines and Other Power Generation Machinery with Multi-Axis Inspection Scope", now U.S. Pat. No. 8,713,999, issued May 6, 2014, and claims priority to U.S. provisional patent application Ser. No. 61/692,393, filed Aug. 23, 2012, and entitled "Hybrid Scope—Turbine Combustor Hardware Visual Inspection Tooling That Can Also Be Used To Inspect The Row 1 Turbine Blades While They Are On Turning Gear (1-1000 rpm)", and claims priority to U.S. provisional patent application Ser. No. 61/692,409, filed Aug. 23, 2012, and entitled "Vision Scope—3D Scanner Tip for Visual Inspection and Measurement", the entire contents of each of which are incorporated by reference herein.

TECHNICAL FIELD

The invention relates to non-destructive, visual inspection of power generation machinery, such as gas turbine engines. More particularly, the invention relates to visual inspection of power generation machinery, such as gas turbine engines with an inspection system, having a single-axis inspection scope and spherical camera. The inspection scope with camera is inserted into an inspection port of the machine. In some embodiments, the inspection scope has anti-rotation extension tracks between nested extension tubes, for ease of extension and retraction of the camera during visual inspections of power generation machinery.

BACKGROUND

As described in U.S. Pat. No. 8,713,999, issued May 6, 2014, and entitled "System and Method For Automated Optical Inspection of Industrial Gas Turbines and Other Power Generation Machinery with Multi-Axis Inspection Scope", power generation machinery, such as generators, or steam or gas turbine engines, are often operated continuously with scheduled inspection and maintenance periods, at which time the machine is taken off line and shut down, for inspection and repair of any components identified during the inspection. Further description herein will focus on exemplary gas turbine engine inspection. Once cooled, the now static gas turbine engine is inspected with optical camera inspection systems. Inspection scope embodiments shown and described in U.S. Pat. No. 8,713,999 incorporate multi-axis inspection scopes, which facilitate selective orientation of an optical inspection camera field of view within the engine, through rotation and articulation of jointed scope segments. In some embodiments, described in U.S. Pat. No. 8,713,999, the inspection scope has a single translation axis, with the ability to rotate the camera field of view 360 degrees. Single translation axis, rotating field of view scope embodiments are described as useful for insertion between blade and vane rows in a turbine engine.

SUMMARY OF INVENTION

The present inventors recognized a need to develop an optical camera inspection system with a small diameter component envelope, for insertion into relatively small engine inspection ports of diameters as little as 1.709 inches (43.41 millimeters). Thus, with use of exemplary embodiments described herein, any ports, or other passages, greater than 43.41 millimeters is a potential scope insertion sites, such as combustor pilot nozzle passages. Exemplary embodiments described herein utilize anti-rotation extension tracks between nested scope extension tubes. Other exemplary embodiments described herein incorporate a bendable knuckle between the extension tubes and the inspection camera, for reducing axial length of the inspection scope as it is maneuvered about confines of the inspected engine. In some embodiments, the bendable knuckle is spring-loaded or otherwise biased, to return the camera body in axial alignment with the extension tubes.

Exemplary embodiments of the optical inspection scopes of the present invention are insertable into engine, or other power generation machinery, inspection ports, or other potential scope insertion sites, as small as 1.709 inches (43.41 millimeters). Internal components of the machine, such as a gas turbine engine, are inspected with a spherical optical camera inspection system mounted on a compact diameter, single-axis inspection scope. The scope, including the camera is capable of insertion within an inspection port or other accessible insertion site. The inspection scope includes nested, non-rotatable telescoping tubes, which define an extension axis. In some embodiments, the circumscribing tubes of the telescoping tubes have anti-rotation collars, which are in sliding engagement with a mating axial groove on an outer circumferential surface of a circumscribed tube. In some embodiments, the mating anti-rotation collar incorporates one or more ball bearings, which engage the corresponding axial groove and in combination form a linear sliding bearing. In other embodiments, one of the mating tubes defines a linear track, which is received in a mating groove defined by one or more anti-rotation collars in the other mating tube. The spherical camera has a 360-degree field of view, and captures internal images of the engine or other power generation machine, without rotation about the scope extension axis. In some embodiments, a bendable knuckle is interposed between the scope extension tubes and the spherical camera, for reducing axial length of the inspection scope assembly while maneuvering it into position about the inspected engine. In some embodiments, the bendable knuckle is spring-loaded or otherwise biased, to return the camera body in axial alignment with the extension tubes. The camera is advanced and/or retracted along a scope extension axis by nested, drive tubes, which incorporate at least one external drive screw on a circumscribed drive tube and corresponding female threads formed in a mating, circumscribing drive tube. In some embodiments, the camera field of view is advanced within the inspected machine, and images are captured at respective advancement positions. In some embodiments, an image processing system combines the respective images into a navigable composite image.

In some embodiments, a distal portion of the rotatable drive hub is oriented within the proximal end of the first telescoping tube, and engaged within the first drive tube, while a proximal portion of the drive hub is coupled to a driven gear that is external the first telescoping tube. In this particular embodiment, a first drive gear is engaged with the driven gear, for rotating the driven gear and the drive hub. A drive apparatus is coupled to the first drive gear, such as a hand crank or an electric motor. Some embodiments incorporate in parallel hand crank and electric motor drives, each coupled to its own drive gear. In some embodiments, one or more anti-rotation collars retain a ball bearing that is in engagement with a corresponding axial groove formed within the outer circumference of a mating, circumscribed, telescoping tube, which in combination comprise a linear bearing assembly. In some embodiments, the camera is retained within a camera housing that is coupled to the camera-mounting collar. In some embodiments, the camera housing also includes an illumination system, such as an array of light emitting diodes ("LEDs"). In some embodiments, the system includes a position encoder, for correlating hub rotation with axial displacement of the camera field of view; and an image processing system coupled to the camera and the position encoder, for storing plural images taken at different camera axial displacement positions, and for combining plural inspection images into a composite image. The inspection scopes, in some embodiments, comprise more than two telescoping tubes and/or more than two nested drive tubes.

Some embodiments are directed to a method for internal inspection of a power generation machine. In practicing the method, a system for inspection of a power generation machine is provided. The system includes a single-axis, extendable inspection scope, which defines an extension axis, for insertion into an inspection port of a power generation machine. The provided scope has first, and second nested, telescoping tubes, respectively having proximal and distal ends and axial length. First and second nested drive tubes are retained within the telescoping tubes, respectively having proximal and distal ends and axial length. The first drive tube has a first drive bushing coupled to the distal end thereof, both of which are rotatable within the telescoping tubes. The first drive bushing defines a bore with female drive threads. The second drive tube defines external male drive threads in engagement with the first drive bushing female threads. The scope also has a camera-mounting collar rigidly coupled to the respective distal ends of the second telescoping tube and the second drive tube, preventing relative rotation thereof. A rotatable drive hub is coupled to the proximal end of the first drive tube, for selective rotation thereof. A mounting flange is coupled to the first telescoping tube, for affixation to an inspection port of a power generation machine. A spherical camera, having a 360-degree field of view, is coupled to the camera-mounting collar, for insertion into a power generation machine and capture of inspection images therein. In some embodiments, the first and second nested, telescoping tubes incorporate anti-rotation features. In some embodiments, the anti-rotation features include a groove on one of the tubes, which receives a bearing that is retained in a collar mounted on the opposing tube. In other embodiments, the anti-rotation features include a track on one of the tubes, which is engaged by a groove formed in a collar mounted on the opposing tube. In some embodiments, a knuckle is interposed between a distal end of the telescoping tubes and the camera-mounting collar. In practicing the method, the provided inspection scope's mounting flange is affixed to an inspection port of a power generation machine, or other inspection entry site of the machine, while inserting the inspection scope therein.

Thereafter the drive hub is rotated, thereby rotating the first drive tube, which in turn advances the second drive tube and the camera field of view within the power generation machine, without rotating the camera about the extension axis of the inspection scope. Respective camera images within the power generation machine are captured at plural positions, as the camera field of view is advanced within the machine.

Exemplary embodiments of the invention feature a system for internal inspection of a power generation machine. The inspection system includes a single-axis, extendable inspection scope, for insertion into an inspection port of a power generation machine. The extendable extension scope includes first, and second nested, telescoping tubes, respectively having proximal and distal ends, inner and outer circumferential surfaces, and axial length. The second telescoping tube has a coaxially oriented linear track on its inner or outer circumferential surface. The first telescoping tube has a first anti-rotation collar coupled proximal the distal end thereof, which defines a groove that is in sliding engagement with the linear track of the second telescoping tube. The first and second nested drive tubes are retained within the telescoping tubes, respectively having proximal and distal ends and axial length. The first drive tube has a first drive bushing coupled to the distal end thereof, both of which are rotatable within the telescoping tube; the first drive bushing defines a bore with female drive threads. The second drive tube defines external male drive threads, which are in engagement with the first drive bushing female threads. A camera-mounting collar is rigidly coupled to the respective distal ends of a circumscribing one of the first or the second telescoping tubes and the second drive tube, preventing relative rotation thereof. A rotatable drive hub is coupled to the proximal end of the first drive tube, for selective rotation thereof. A mounting flange is coupled to the circumscribing one of the first or the second telescoping tubes, for affixation to an inspection port of a power generation machine. A spherical camera, having a 360-degree field of view, is coupled to the camera-mounting collar, for insertion into a power generation machine and capture of inspection images.

Other exemplary embodiments of the invention feature a system for internal inspection of a power generation machine. The inspection system includes a single-axis, extendable inspection scope, which defines an extension axis, for insertion into an inspection port of a power generation machine. The inspection scope includes first, second, third, and fourth nested, telescoping tubes, respectively having proximal and distal ends and axial length. The second, third and fourth telescoping tubes respectively have a coaxially oriented linear track on an outer circumferential surface thereof. The first telescoping tube has a first anti-rotation collar coupled proximal the distal end thereof, in sliding engagement with the linear track of the second telescoping tube. The second telescoping tube has a second anti-rotation collar coupled proximal the distal end thereof, in sliding engagement with the linear track of the third telescoping tube. The third telescoping tube has a third anti-rotation collar coupled proximal the distal end thereof, in sliding engagement with the linear track of the fourth telescoping tube. The first, second and third nested drive tubes are retained within the telescoping tubes; they respectively have proximal and distal ends and axial length. The first drive tube has a first drive bushing coupled to the distal end thereof, both of which are rotatable within the fourth telescoping tube. The first drive bushing defines a bore with female drive threads. The second drive tube defines external male threads, in engagement with the first drive bushing female threads. The second drive tube has a second drive bushing coupled to the distal end thereof, both of which are rotatable within the fourth telescoping tube. The second drive bushing defines a bore with female drive threads. The third drive tube defines external male threads in engagement with the second drive bushing female threads. A camera-mounting collar is rigidly coupled to the respective distal ends of the fourth telescoping tube and the third drive tube, preventing relative rotation thereof. A rotatable drive hub is coupled to the proximal end of the first drive tube, for selective rotation thereof. A mounting flange is coupled to the first telescoping tube, for affixation to an inspection port of a power generation machine. A spherical camera, having a 360-degree field of view, is coupled to the camera-mounting collar, for insertion into a power generation machine and capture of inspection images.

Additional exemplary embodiments of the invention feature methods for internal inspection of a power generation machine. The featured method is practiced by providing a system for inspection of a power generation machine. The provided inspection system includes a single-axis, extendable inspection scope, for insertion into an inspection port of a power generation machine. The extendable inspection scope has first, and second nested, telescoping tubes, respectively having proximal and distal ends, inner and outer circumferential surfaces, and axial length. The second telescoping tube has a coaxially oriented linear track on its inner or outer circumferential surface. The first telescoping tube has a first anti-rotation collar coupled proximal the distal end thereof, which defines a groove that is in sliding engagement with the linear track of the second telescoping tube. The first and second nested drive tubes are retained within the telescoping tubes, respectively having proximal and distal ends and axial length. The first drive tube has a first drive bushing coupled to the distal end thereof, both of which are rotatable within the telescoping tubes; the first drive bushing defines a bore with female drive threads. The second drive tube defines external male drive threads in engagement with the first drive bushing female threads. A camera-mounting collar is rigidly coupled to the respective distal ends of a circumscribing one of the first or the second telescoping tubes and the second drive tube, preventing relative rotation thereof. A rotatable drive hub coupled to the proximal end of the first drive tube, for selective rotation thereof. A mounting flange is coupled to the circumscribing one of the first or the second telescoping tubes, for affixation to an inspection port of a power generation machine. A spherical camera, having a 360-degree field of view, is coupled to the camera-mounting collar, for insertion into a power generation machine and capture of inspection images. The method is practiced by affixing the mounting flange to an inspection port, or other machine-inspection entry site in a power generation machine, while inserting the inspection scope therein. The drive hub is rotated, thereby rotating the first drive tube, and advancing the second drive tube and the camera field of view within the power generation machine, without rotating the camera about the inspection scope extension axis. Camera images are captured within the power generation machine at plural positions, as the camera field of view is advanced within the machine.

Features of the exemplary embodiments of the invention described herein may be applied jointly or severally, in any combination or sub-combination.

BRIEF DESCRIPTION OF DRAWINGS

The exemplary embodiments of the invention can be understood by considering the following detailed description in conjunction with the accompanying drawings, in which:

FIG. 2 is a top perspective view of a controller box of the inspection scope of FIG. 1;

FIG. 3 is an end perspective view of the controller box of FIG. 2, after removal of a gear cover, showing drive gears and a driven gear;

FIG. 4 is a top perspective view of the controller box of FIG. 2, after removal of outer covers, showing a motorized drive gear and a manually-cranked drive gear engaging the driven gear;

FIG. 5 is an axial cross-sectional view through telescoping tubes and drive tubes of the inspection scope of FIG. 1;

FIG. 6 is a detailed, fragmentary axial cross-sectional view through an outer telescoping tube and a rotatable drive hub at a proximal end of the inspection scope of FIG. 5;

FIG. 7 is a detailed, fragmentary axial cross-sectional view through all of the telescoping tubes and drive tubes, at a distal end of the inspection scope of FIG. 5;

FIG. 8 is an elevational axial cross sectional view of the inspection scope of FIG. 7, oriented normal to the view of FIG. 7, and taken through an anti-rotation collar of a first or outer telescoping tube;

FIG. 9 is a cross-sectional view of an anti-rotation collar of the scope of FIG. 1, taken through 9-9 of FIG. 8;

FIG. 10 is a top plan view of a camera housing of the scope of FIG. 1;

FIG. 11 is a perspective view of a camera head of FIG. 1;

To facilitate understanding, identical reference numerals have been used, where possible, to designate identical elements that are common to the figures. The figures are not drawn to scale.

DESCRIPTION OF EMBODIMENTS

Exemplary embodiments are utilized for inspection of internal components of power generation machinery, such as gas turbine engines. The engine internal components are inspected with a spherical optical camera inspection system mounted on a compact diameter, single-axis inspection scope that is capable of insertion within an inspection port or other accessible insertion site. In some embodiments, the inspection scope, with camera, is inserted through a combustor pilot port, through the corresponding combustor transition and stopping before the row 1 vanes, with a view of the row 1 blades and vanes. The system is capable of capturing images along the camera translation path. Plural images are combined to generate a composite image of components within the inspection path. In some embodiments, the composite image is navigable, analogous to "street view" geographic path images available on some Internet-based map and trip navigation sites.

The inspection scope includes nested, non-rotatable telescoping tubes, which define an extension axis. Circumscribing, telescoping tubes have anti-rotation collars, which are in sliding engagement with a mating axial groove on an outer circumferential surface of a circumscribed tube, with the groove and collar forming a linear slide. In other embodiments, the telescoping tubes have anti-rotation collars, which are in sliding engagement with a mating track formed on an inner or outer circumferential surface of one of the engaging tubes. The camera is advanced and/or retracted along a scope extension axis by nested, drive tubes, which incorporate at least one external drive screw on a circumscribed drive tube and corresponding female threads formed in a mating, circumscribing drive tube. In some embodiments, the female threads are formed in a drive bushing coupled to the corresponding drive tube. The spherical camera has a 360-degree field of view, and captures images without rotation about the scope extension axis. In some embodiments, a bendable knuckle is interposed between the spherical camera and the scope extension tubes, for collapsing axial length of the inspection scope as it is maneuvered around the inspected engine. In some embodiments, the bendable knuckle is spring loaded.

Figure 1:
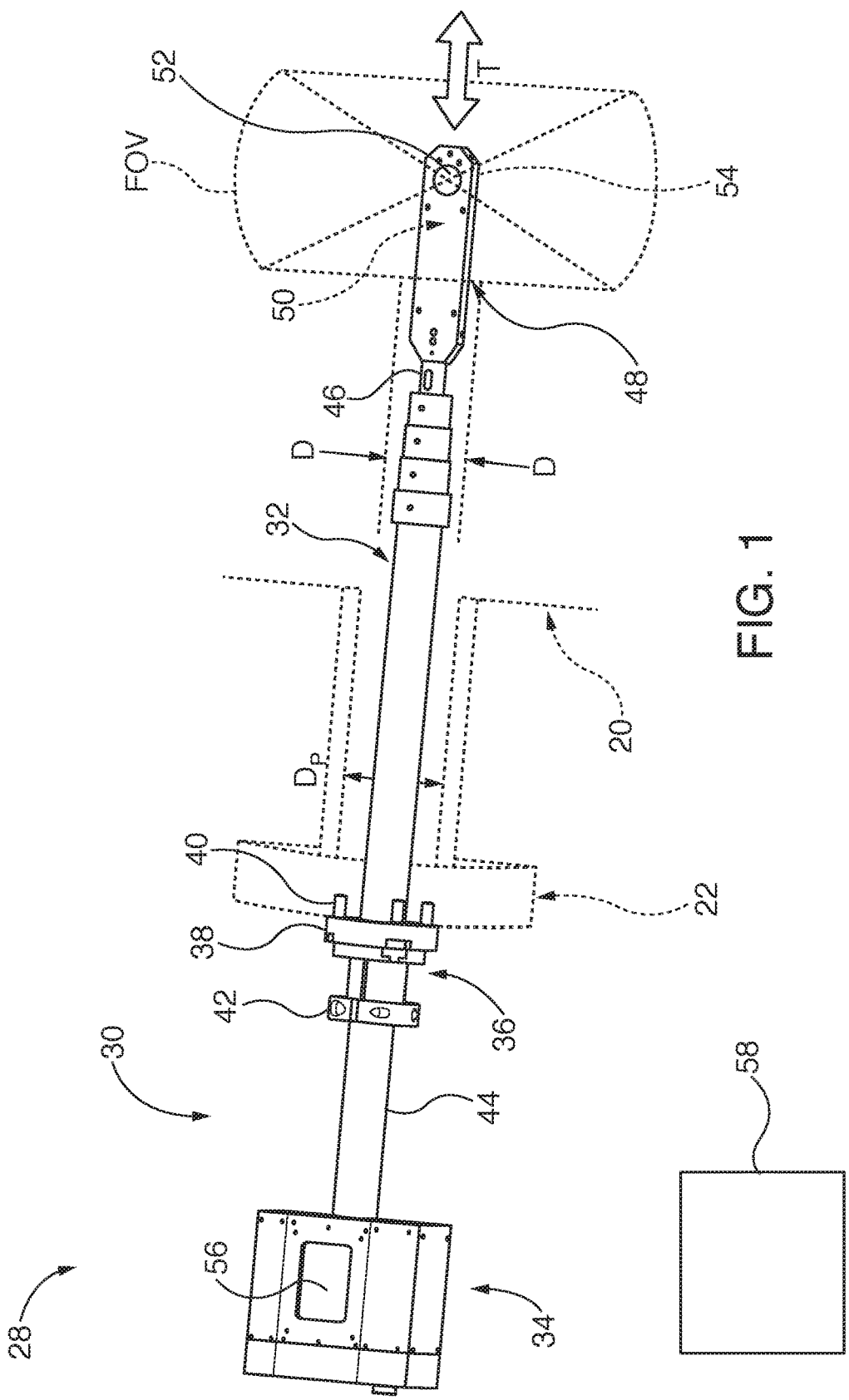
FIG. 1 is a top plan view of an embodiment of an inspection scope of the invention inserted within an inspection port of a power generation machine, such as an inspection port of a gas turbine engine.

FIG. 1 shows an exemplary power generation machine, such as a gas turbine engine 20, which includes an inspection port 22, with an internal passage minimum clearance diameter $D_p$. The term "port" as used herein includes dedicated inspection ports, which are sealed after completion of inspections, or any other type entry aperture that allows passage of an inspection scope into the engine interior. Other types of exemplary entry apertures or inspection access sites include a combustion pilot nozzle insertion aperture within a combustor, or a manway access cover of a gas turbine engine. The exemplary inspection system 28 includes an inspection scope 30, which has a telescoping portion 32 for insertion into the engine 20, a controller box 34 remains outside the engine. The inspection scope 30 includes a mounting collar 36 coupled to the telescoping portion 32, with a mounting flange 38 that is affixed to the inspection port 22 by fasteners 40. The mounting collar 36 includes a mounting collar-retaining clamp 42 that is clamped adjustably along an exterior surface of an outer or first telescoping tube 44. The retaining clamp 42 is selectively positioned and clamped axially relative to the first telescoping tube 44, as needed or desired for any particular inspection procedure. A camera-mounting collar 46 is coupled to a distal end of the inspection scope-telescoping portion 32, and is coupled to a camera housing 48. The camera housing 48 retains a spherical camera 50, which has a 360 degree field of view ("FOV"), for capturing images of components within the engine 20, without the need to rotate (pan) the camera FOV about an extension axis of the inspection scope telescoping portion 32. The spherical camera 50 has a first camera lens 52 on one side of the camera housing 48, and a second camera lens 54 on the other side of the camera housing, which in this particular embodiment is oriented 180 degrees opposite the first camera lens 52. The inspection scope 30 includes a visual display 56 retained within the controller box 34, for real-time monitoring of images being captured by the camera 50, or for retrieval of previously captured and stored images. Optionally, camera images are viewed remotely, and the inspection scope controlled remotely by an external computing device, such as a tablet computer 58. The tablet computer 58 communicates with the inspection scope 30 by hardwire cable (not shown) or by a wireless communication pathway. The inspection scope-telescoping portion 32 and the camera housing 48 have a maximum outside diameter D, which is smaller than the port minimum clearance diameter $D_p$. Working embodiments of the inspection scope have been constructed with a maximum outside diameter of 1.68 inches (42.67 millimeters) and a telescopic extension range of 48 inches (1220 millimeters) along an extension axis T.

FIGS. 2-4 show the controller box 34, with a fragmentary view of proximal portions of the inspection scope-telescoping portion 32 and its first or outer telescoping tube 44. The controller box 34 has a removable gear cover 60, and an externally accessible hand crank socket 62, for selective coupling to a hand crank 69. Toothed driven gear 64 engages mating teeth of the first drive gear 66, which has a drive-gear hub extension 68 that is coupled to the external hand crank socket 62. In FIG. 4, the hand crank 69 is shown directly coupled to the drive gear 64, without the gear cover 60 or the hand crank socket 62, to illustrate how the scope telescoping portion 32 is advanced or retracted along the telescoping extension axis/dimension T, by rotation of the drive gear 64. The inspection scope 30 also has a motorized drive for advancing and retracting the telescoping portion 32, which operates in parallel with and independently from the manual or hand-cranking drive. The toothed, second drive gear 70 engages mating teeth of the driven gear 64. Electric motor 72, which is a known motor used in motion control systems, drives the second drive gear 70. In this embodiment, the motor 72 incorporates a rotary positon encoder, which generates encoder data indicative of the number of motor shaft turns. The inspection scope 30 converts rotary motions R of the driven gear 64 into linear translation T of the telescoping portion 32. Thus, the rotary motion of the motor drive shaft and the position encoder data are correlated with linear translation of T of the telescoping portion 32. Other types of known position encoders can be substituted for the motor internal position encoder 74. The driven gear 64 is coupled to a rotatable drive hub 76, so that rotation of the drive gear 64 by either the first drive gear 66 or the second drive gear 70 also rotates the drive hub 76.

FIGS. 1 and 5-9 show internal construction of the inspection scope-telescoping portion 32. A proximal end of the telescoping portion 32 retains the driven gear 64 and the rotatable hub 76, while the camera-mounting collar 46 and camera housing mounting screw 78 are oriented on its distal end. The first or outer telescoping tube 44 retains a drive hub roller bearing 80 and a hub support bushing 82, for mounting of the rotatable hub 76, as well as a drive tube support bushing 84, for retention of a first or outer drive tube 86. The first drive tube is coupled to the rotatable hub 76 by first pin 88. Rotation of the driven gear 64 in the clockwise or counterclockwise directions R in turn rotates the hub 76 and the first drive tube 86. Interconnection of the first drive tube 86 to other downstream, distal second 112 and third 122 drive tubes, and their operation is described greater detail later herein.

The inspection scope-telescoping portion 32 comprises first or outer 44, second 92, third 96 and fourth 100 nested telescoping tubes, which in turn retain nested first or outer 86, second 112, and third or inner 122 drive tubes. Advancement or retraction of the drive tubes and telescoping tubes adjusts the axial length T of the inspection scope-telescoping portion 32. The telescoping tubes 44, 92, 96 and 100 incorporate anti-rotation structural features, which prevent rotation of the camera housing 48 about the extension axis of the telescoping portion 32. Each abutting pair of telescoping tubes incorporates one or more linear bearings, with the circumscribing telescoping tube including an anti-rotation collar and one or more retained ball bearings, which ride in a mating axial groove formed in the outer circumference of the circumscribed telescoping tube. The compact linear bearing construction facilitates relatively small maximum diameter D of the telescoping tubes and collars of 1.68 inches (42.67 millimeters). More particularly, the first telescoping tube 44 has a first anti-rotation collar 90, which engages a corresponding axial groove formed in the second telescoping tube 92. In turn, the second telescoping tube has a second anti-rotation collar 94, which engages an axial groove formed in the third telescoping tube 96. The third telescoping tube 96 in turn has a third anti-rotation collar 98, which engages an axial groove formed in the fourth or inner telescoping tube 100. A fourth tube collar 102 is rigidly coupled to the fourth telescoping tube 100, which in turn rigidly couples that tube to the camera mounting collar 46. Screws 124 in turn rigidly couple the camera mounting collar 46 to the third or inner drive tube 122, so that the camera housing 48 does not rotate about the extension axis of the inspection scope's telescoping portion 32. Rigid affixation of the third drive tube 122 to the camera mounting collar 46 facilitates routing of cables between the camera housing 48 and the controller box 34, through the third drive tube's lumen 126 and apertures 128 formed in the camera mounting collar 46.

Structure and operation of the first 86, second 112 and third or inner 122 drive tubes is now described, with reference to FIGS. 6-8. As previously described, rotation of the rotatable hub 76 in either direction R rotates the first or outer drive tube 86, which are interconnected by the first pin 88. A first drive bushing 104 is rigidly coupled to a distal end of the first drive tube 86, by a first drive bushing-pin 106. The first drive bushing 104 and the first drive tube 86 are freely rotatable within the inner lumen of the fourth or inner telescoping tube 100. The first drive bushing 104 defines internal female drive threads (e.g., Acme profile drive threads) 108, which engage corresponding male external drive threads 110 formed on the outer circumference of the second drive tube 112. Rotation of the first drive tube 86 advances the external drive threads 110 relative to the rotating first drive bushing 104, thus advancing the second drive tube to the right in FIG. 8, along the extension axis T. A rotation stop is incorporated in the proximal end of the second drive tube 112, such as a pin or screw driven into a trough in the threads 110 profile, in order to prevent axial separation between the first 86 and second 112 drive tubes. When the second drive tube 112 proximal-end rotation stop contacts the first drive bushing 104, further rotation of the rotatable hub 76 also commences rotation of the second drive tube.

A distal end of the second drive tube 112 incorporates a rigidly mounted second drive bushing 114, which are rigidly connected to each other by second drive bushing-pin 116. The second drive bushing 114 defines female threads, which engage corresponding male external threads 118 on the outer circumference of the third or inner drive tube 122. The second drive bushing 114 and the second drive tube 112 are freely rotatable within the inner lumen of the fourth or inner telescoping tube 100. The second drive bushing 114 defines internal female drive threads (e.g., ACME profile drive threads) 108, which engage corresponding male external drive threads 120 formed on the outer circumference of the third drive tube 122. Rotation of the second drive tube 112 with first drive tube 86 advances the external drive threads 120 relative to the rotating second drive bushing 114, thus advancing the third drive tube 122 to the right in FIG. 8, along the extension axis T. A rotation stop is incorporated in the proximal end of the third drive tube 122, such as a pin or screw driven into a trough in the threads 120 profile, in order to prevent axial separation between the second 112 and third or inner 122 drive tubes. The inner drive tube 122 is rigidly coupled to the camera-mounting collar 46 and the fourth or inner telescoping tube 100. The inner drive tube cannot rotate relative to the extension axis T.

FIGS. 8 and 9 show in detail the linear bearing structure that prevents relative rotation among the telescoping tubes 44, 92, 96 and 100. Focusing on the mating interface between the circumscribing first telescoping-tube 44 and its abutting, inscribed, second telescoping-tube 92, the latter has axial groove 132, which is parallel to the extension axis of the inspection scope. The axial groove 132 terminates inboard of the proximal and distal ends of the second telescoping tube 92, in order to prevent axial separation from the first telescoping tube 44. The first anti-rotation collar 90 retains ball bearings 134, which are in engagement with the axial groove 132. Respective ball bearing tensioning screws 136 selectively adjust the ball bearing 134 pressure against the mating axial groove 132. The respective second 94, and third 98 anti-rotation collars incorporate the same linear bearing construction, with mating axial groove in the circumscribed, inner mating tube (including axial separation prevention during tube extension) and ball bearing, as the first anti-rotation collar 90. All of the aforementioned anti-rotation collars are affixed to its corresponding telescoping tube by retention screws 138.

FIGS. 8, 10, and 11 show further structural details of the camera housing 48. The camera housing 48 as coupled to the camera-mounting collar 46 by housing mounting screw 78. The housing 48 retains the spherical camera 50, and defines apertures for the camera lenses 52 and 54 on opposite sides of the housing. In this exemplary embodiment, the spherical camera 50, with 360-degree field of view, is an off-the-shelf, commercially available camera with corresponding operation software, such as a model Theta S camera, manufactured by Ricoh Company, Ltd. of Tokyo Japan, and sold by Ricoh USA, Inc. of Malvern Pa. USA. The camera housing 48 also provides apertures 128 for retention of illumination light emitting diodes ("LEDs"). LED cable 146 and camera cable 148 pass through the third drive tube lumen 126 and the camera mounting collar apertures 128, and are then wrapped about a shank portion of the mounting collar 46, in order to provide strain relief protection for the connections of those cables to the respective LED 140 and camera 50.

Figure 12:
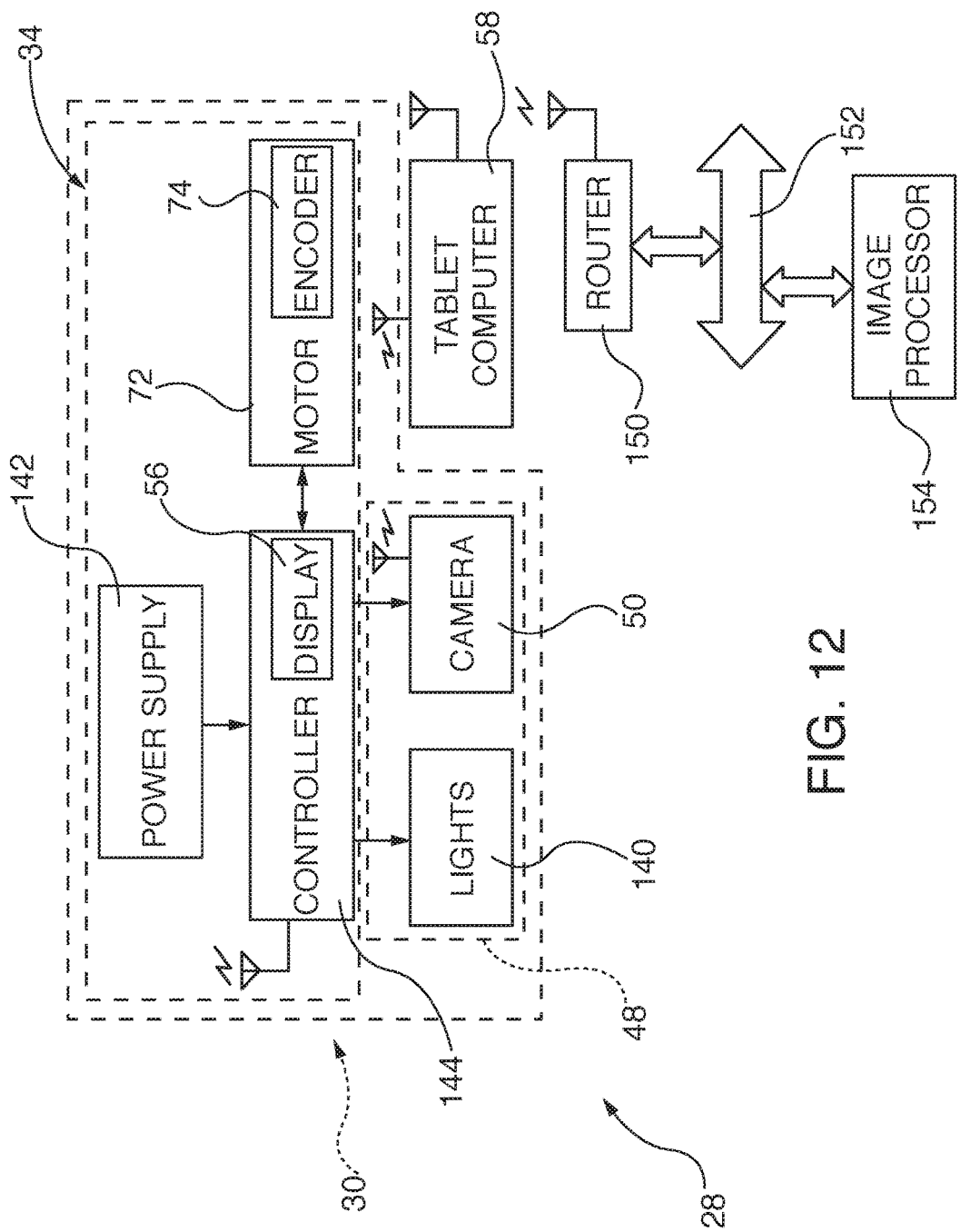
FIG. 12 is block diagram of the electrical circuits incorporated into the inspection scope of FIG. 1.

The block diagram of FIG. 12 shows interoperable connection of components and subsystems within the inspection system 28. Electro-mechanical structures of the inspection scope 30, the control box 34, and the camera housing 48 are shown schematically in dashed lines. Power supply 142, shown here for illustrative purposes within the control box 34, provides power for the controller 144, the display 56, the motor 72 and its encoder 74, the lighting system 140 and the camera 50. The controller 144 controls the lighting 140, camera 50, motor 72 and in some embodiments receive encoder data from the encoder 74. In some embodiments, the controller 144 has wireless communication capability for direct or indirect communication via a known wireless router 150 or via any known form of data communications network, including the Internet. In some embodiments, the controller 144 and/or the camera 50 are in wireless or hard-wired communication with the tablet computer 58 or an image processor 154 or any other type of known workstation.

Referring to FIGS. 1, 3, and 12, the inspection system 28 is used to inspect internal structure of a power generation machine 20, such as a gas turbine engine, by affixing the inspection scope 30 mounting flange 38 to an inspection port 22 or other machine inspection entry site, while inserting the inspection scope telescoping portion 32, including the camera housing 48 into the machine's interior. Once the inspection scope 30 is positioned for inspection, the camera housing 48 is advanced into the machine by rotating the driven gear 64 and its attached drive hub 76 with a hand crank 69 that is coupled to the controller box 34, or by operating the self-contained internal motor 72, thereby rotating the first drive tube 86, and advancing the second 112 and/or third 122 drive tube and ultimately the camera housing 48, with its spherical, 360 degree camera 50 within the power generation machine, along the inspection scope extension axis T, without rotating the camera 50 about the extension axis T. The 360-degree images generated within the camera field of view are captured in one or more positions along the extension axis T.

In many inspection embodiments, camera 50 images are captured at plural positions along the extension axis T. In embodiments where the inspection scope 30 is provided with a position encoder, such as the position encoder 74 of the motor 72, the encoder generates position output data that is correlated with axial displacement of the camera 50 field of view along the extension axis T. An image processing system in the controller 144, remote tablet or other computer 58 or in a remote, dedicated image processing workstation 154 determines axial displacement position of the camera field of view with the position encoder 74 output data, and correlates the determined axial displacement position T with a corresponding position within the corresponding camera image. Correlation of encoder 74 output position data with an image is performed with known, commercially available data acquisition hardware, and software. In some embodiments, the controller 144, and/or remote computers, such as the tablet computer 58, and/or the image processing system 154 archive images and/or encoder position data. In some embodiments, real-time and/or archived images are also viewable on the display 56 of the controller box 34. In some embodiments, the controller 144 automatically controls advancement of the camera housing 48 along the extension axis T by controlling the motor 72 in a feedback loop with the encoder 74.

In some embodiments, the image processing system, wherever located, combines plural inspection images into a navigable composite image, which is analogous to "street view" geographic mapping that is available in some Web-based applications. Commercially available image combining, and image-navigation software packages, operable on controller and/or computer hardware platforms, include the krpano Panorama Viewer, which is available from krpano Gesellschaft mbH of Deutschkreutz, Austria.

While reference to an exemplary controller 144 or tablet computer 58, or remote workstation 154 platform architecture, and implementation of operational tasks by software modules executed by the respective device's internal processor, it is also to be understood that exemplary embodiments of the invention are implemented in various forms of hardware, software, firmware, special purpose processors, or a combination thereof. Preferably, aspects of the invention embodiments are implemented in software as a program tangibly embodied on a non-volatile, non-transitory signal, program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. In addition, various other peripheral devices may be connected to the computer/controller platform.

It is to be understood that, because some of the constituent system components and method steps depicted in the accompanying figures are preferably implemented in software, the actual connections between the system components (or the process steps) may differ depending upon the manner in which the exemplary embodiments are programmed. Specifically, any of the computer platforms or devices may be interconnected using any existing or later-discovered networking technology; they may all be connected through a lager network system, such as a corporate network, metropolitan network or a global network, such as the Internet.

Figure 13:
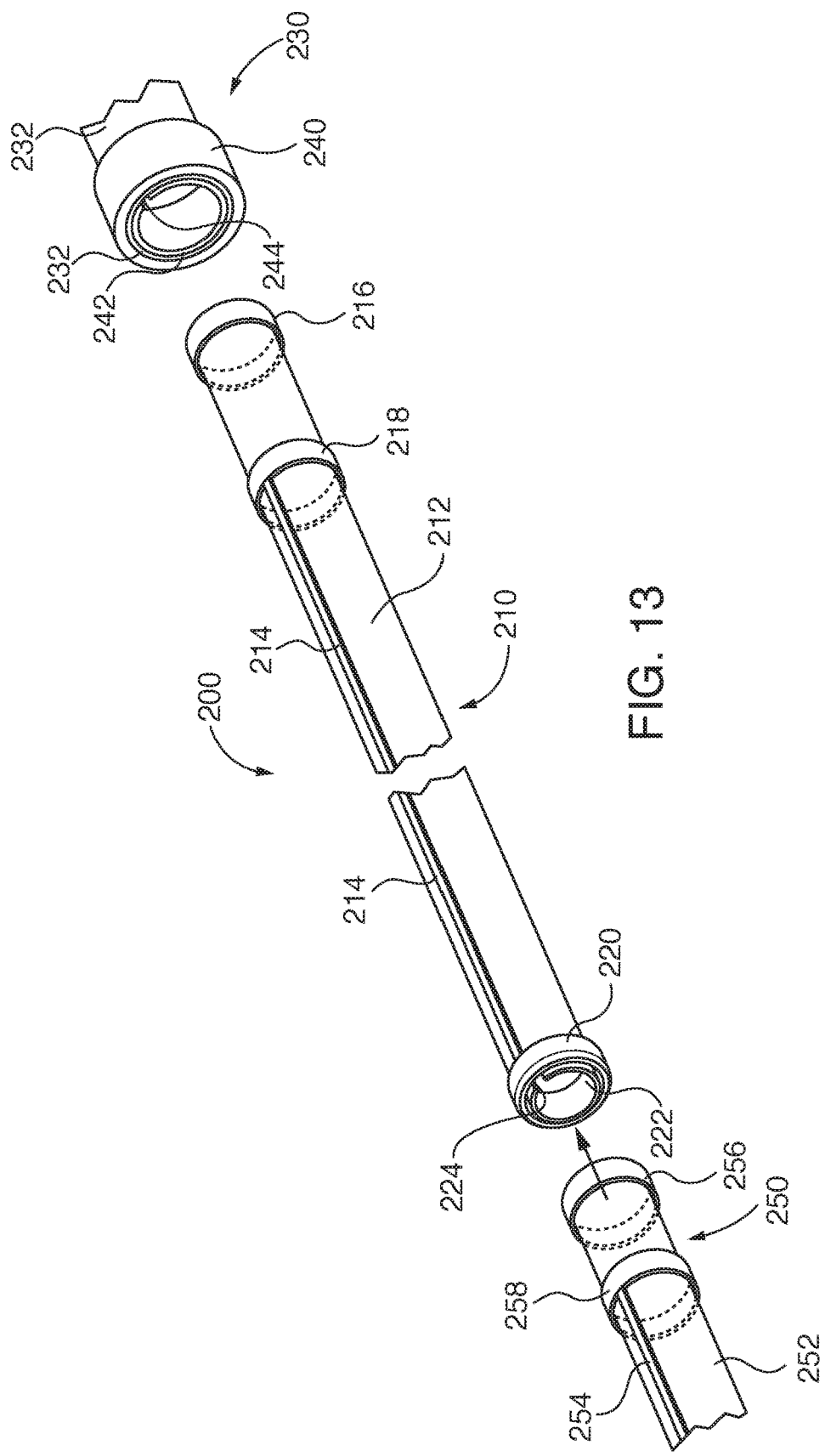
FIG. 13 is an exploded, perspective view of an alternate embodiment of mating, telescoping tubes, which incorporate an anti-rotation track and mating collars.
Figure 15:
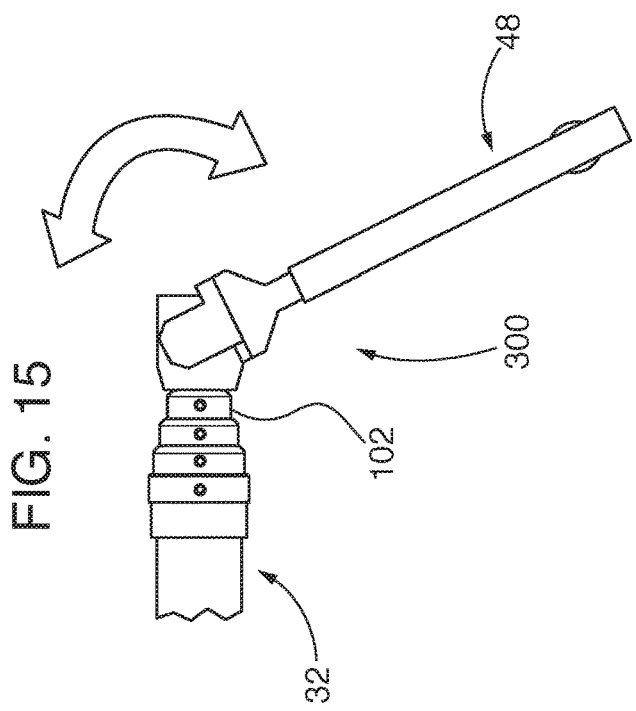
FIG. 15 is a top plan, fragmentary view of an inspection scope of the invention, having a bendable knuckle interposed between the scope extension tubes and the camera.
Figure 14:
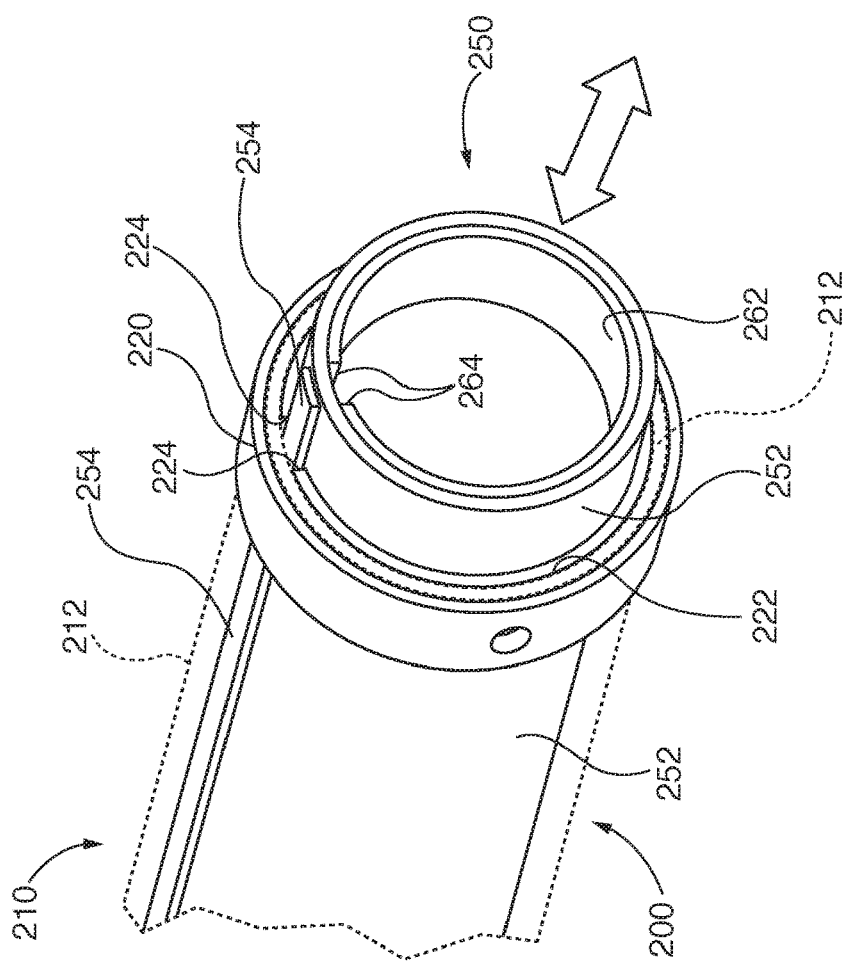
FIG. 14 is a detailed perspective view of the mating, telescoping tubes, anti-rotation track, and mating collars of FIG. 13.
Figure 16:
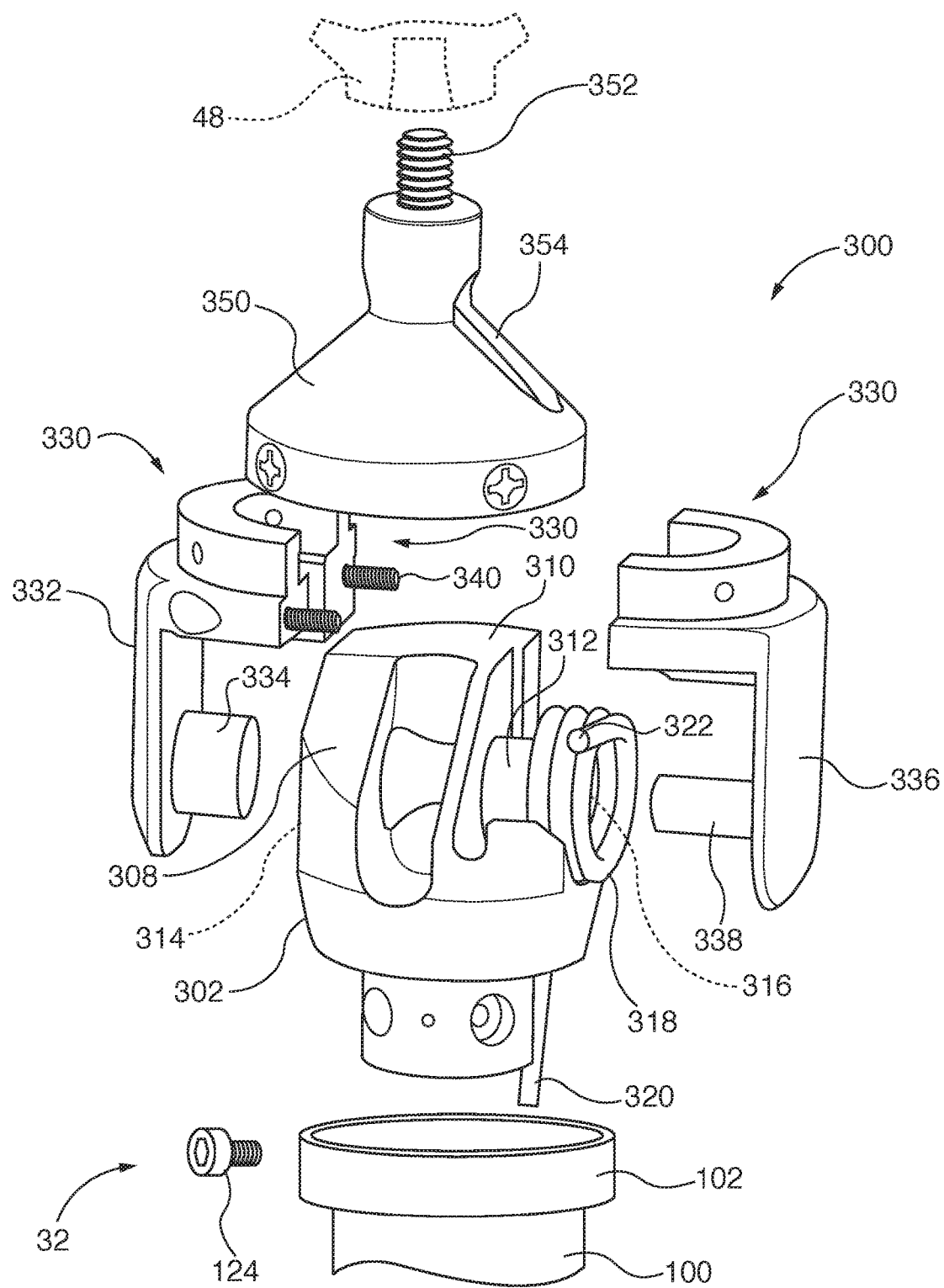
FIG. 16 is an exploded view of the bendable knuckle of FIG. 15.

FIGS. 13 and 14 show an alternate embodiment of a linear track structure that prevents relative rotation among the telescoping tubes, which replaces the linear bearing structure of FIGS. 8 and 9. Recall that in FIGS. 8 and 9, the linear bearing, mating interface, between the circumscribing first telescoping-tube 44 and its abutting, inscribed, second telescoping-tube 92 incorporates the axial groove 132, which is parallel to the extension axis of the inspection scope. In that embodiment, the first anti-rotation collar 90 retains ball bearings 134, which are in engagement with the axial groove 132. The respective second 94, and third 98 anti-rotation collars incorporate the same linear bearing construction, with mating axial groove in the circumscribed, inner mating tube (including axial separation prevention during tube extension) and ball bearing, as the first anti-rotation collar 90.

In the alternative embodiment of FIGS. 13 and 14, telescoping tube anti-rotation or anti-clocking is provided in the telescoping tubes 200, by mating linear tracks on one tube and grooved collars, such as grooved split-collars, on the other, opposed mating tube. Specifically, the intermediate, telescoping tube assembly 210 has an intermediate tube 212, with an externally affixed track 214 that is axially aligned with the inspection scope's extension axis. A radially extending, intermediate stabilizing collar 216 is affixed to an upstream end of the intermediate tube 212. An intermediate extension stop 218 radially extends from the outer circumferential surface of the intermediate tube 212. The intermediate, telescoping tube assembly 210 has an outer collar 220 that is affixed to the downstream end of the outer circumference of the intermediate tube 212. An anti-rotation collar 222 is nested within, and circumscribed by the inner circumferential surface of the intermediate tube 212. The anti-rotation collar 222 is a split-collar, which defines an axially aligned through-groove 224.

The intermediate, telescoping tube assembly 210 is nested within, and circumscribed by an outer, telescoping tube assembly 230. The latter is of similar construction to the intermediate, telescoping tube assembly 210, and includes an outer tube 232, an outer collar 240 that is affixed to the downstream end of the outer circumference of the outer tube 232. An outer, anti-rotation collar 242 is nested within, and circumscribed by the inner circumferential surface of the outer tube 232. The outer, anti-rotation collar 242 is a split-collar, which defines an axially aligned through-groove 244, for mating engagement with the affixed track 214 of the mating, circumscribed, intermediate, telescoping tube assembly 210. Concentric alignment between the intermediate, telescoping tube assembly 210 and its circumscribing outer, telescoping tube assembly 230 is preserved by the respective, radially extending intermediate stabilizing collar 216 and the intermediate extension stop 218. The intermediate extension stop 218 also prevents inadvertent axial separation of the intermediate tube 212 from the outer tube 232, by axially abutting against the anti-rotation collar 242 that is nested within the inner circumference of the outer tube 232. In some embodiments, the intermediate stabilizing collar 216 and the intermediate extension stop 218 are constructed of self-lubricating polymer, for reduction of rubbing friction with the inner circumferential surface of the outer tube 232. In some embodiments, the track 214 is constructed of self-lubricating carbon fiber, and affixed to the intermediate tube 212 with mechanical fasteners and/or adhesive. The track 214 provides additional incremental axial stiffness to the intermediate tube and increased rubbing surface area, for smooth extension and retraction of the nested, telescoping tubes, in cooperation with the intermediate stabilizing collar 216 and the intermediate extension stop 218. If the outer, telescoping tube assembly 230 is configured for insertion within another extension tube, it will incorporate an external track, stabilizing collar and extension stop similar to those of the intermediate, telescoping tube assembly 210.

In FIGS. 13 and 14, an inner, telescoping tube assembly 250 is nested within and has structural features corresponding to those of the intermediate, telescoping tube assembly 230. Specifically, the inner, telescoping tube assembly 250 has an inner tube 252, with an externally affixed track 254 that is axially aligned with the inspection scope's extension axis. A radially extending, inner stabilizing collar 256 is affixed to an upstream end of the inner tube 252. An inner extension stop 258 radially extends from the outer circumferential surface of the inner tube 252. The inner, telescoping tube assembly 250 has an outer collar (not shown) that is affixed to the downstream end of the outer circumference of the inner tube 252. If the inner, telescoping tube assembly is configured to circumscribe and receive another extension tube assembly, it is provided with an inner, anti-rotation collar 262 that is nested within, and circumscribed by the inner circumferential surface of the inner tube 252. The inner, anti-rotation collar 262 is a split-collar, which defines an axially aligned through-groove 264. If the inner, telescoping tube assembly 250 is the innermost extension tube, it need not be provided with the inner, anti-rotation collar 262. Rather, the inner tube 252 is provided with an outer collar and camera mounting structure, similar to the fourth tube collar 102 and the camera-mounting collar 46 of the embodiment shown in FIG. 7.

The embodiments of FIGS. 13 and 14 depict respective circumscribed telescoping tubes 212 and 252, having respective, radially extending, external alignment tracks 214 and 254, which respectively mate with corresponding split-collars 242 and 222 on the respective opposed circumscribing tubes 212 and 230. In other embodiments, the tracks are affixed to an inner circumference of a circumscribing tube; the mating, partial-depth groove or full-depth split collar is affixed to the corresponding outer circumference of the circumscribed, opposed mating tube.

In some embodiments, the camera mounting collar 46 of FIG. 7 is replaced with a bendable knuckle assembly 300, shown in FIGS. 15-18, for reducing total axial length of the inspection scope, such as for easier maneuvering about the engine prior to insertion into an inspection port or an injector pilot nozzle aperture. While the knuckle assembly 300 of FIGS. 15-18 replaces the camera-mounting collar 46 of FIG. 7, in some embodiments, a knuckle assembly incorporates a female threaded aperture, for mating engagement with the existing camera housing mounting screw 78 on the distal end of the camera-mounting collar 46. In such embodiments, where the knuckle assembly is affixed to the camera housing mounting screw 78, the overall axial length of the inspection scope increases by the length of the knuckle assembly.

In FIGS. 15-18, the knuckle assembly 300 comprises a knuckle hub 302, with a male hub collar 304, for insertion into the fourth, inner telescoping tube 100 and the fourth tube collar 102, and affixation by screws 124. The knuckle hub 302 defines a central through bore 306, a ramped hub surface 308, and a hub flat stop-surface 310. A cylindrical stud 312 projects from the knuckle hub 302, perpendicular to the long axis of the through bore 306 and the scope tube extension axis. The cylindrical stud 312 incorporates first bore 314 and second bore 316, respectively oriented on opposed ends thereof. The outer circumferential surface of the cylindrical stud 312 captures a biasing, torsion spring 318, with the spring having a helical-wound portion and respective first 320 and second 322 springtails.

Figure 18:
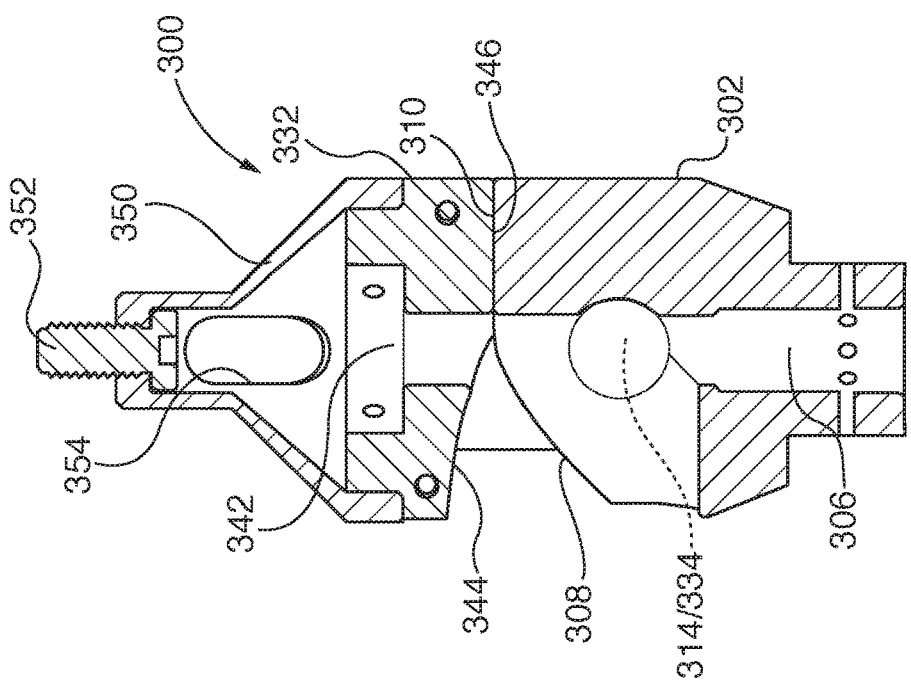
FIG. 18 is an axial cross-sectional view of the bendable knuckle of FIG. 15, in a fully extended state, where ends of the knuckle are axially aligned with the inspection scope axis.
Figure 17:
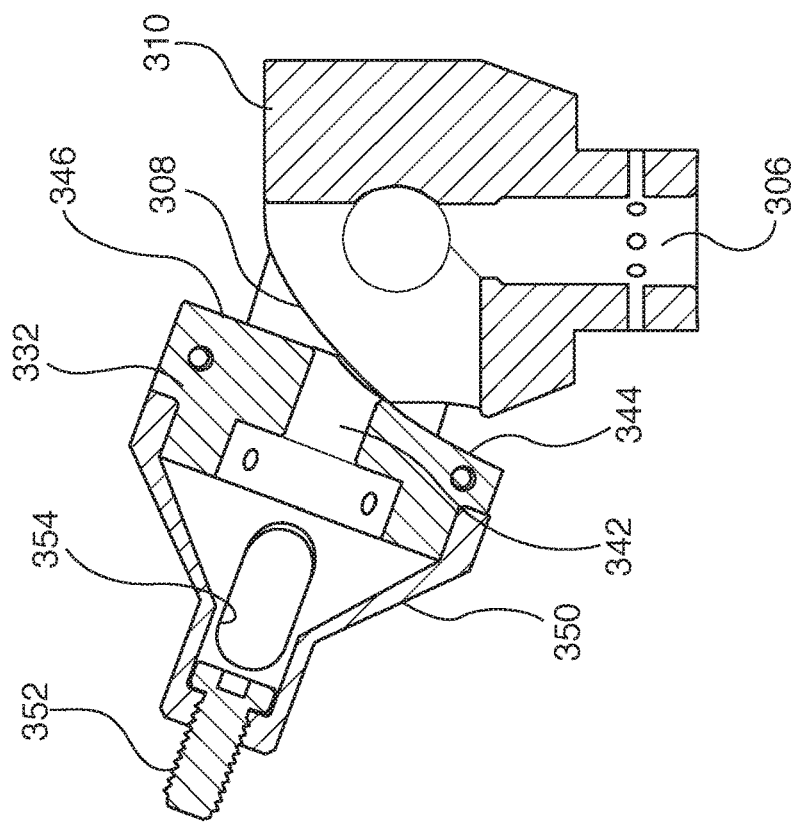
FIG. 17 is an axial cross-sectional view of the bendable knuckle of FIG. 15, in a bent state.

The knuckle assembly 300 has a split yoke assembly 330, which includes a first yoke portion 332, with a first journal bearing 334 that is captured within the first bore 314 of the knuckle hub 302. A second yoke portion 336 has a second journal bearing 338 that is captured within the second bore 316 of the knuckle hub 302. In some alternative embodiments, not shown in the figures, the first and second yoke portions define bores for receipt of journal bearings formed in the male ends of the cylindrical stud of knuckle hub. The first 332 and second 336 yoke portions are affixed to each other with yoke fasteners 340; when they are assembled, the yoke assembly 330 defines a central through bore 342. As shown in FIGS. 17 and 18, each of the first 332 and second 336 yoke portions respectively defines an ramped yoke surface 344, and a yoke flat stop-surface 346, which respectively cooperate with the corresponding ramped hub surface 308, and the hub flat stop-surface 310 of the hub 302 to delimit pivoting travel of the yoke assembly 330 relative to the knuckle hub 302. Selective manual manipulation and bending of the knuckle assembly 300 into the position of FIG. 17 is resisted by the biasing force imparted by the torsion spring 318, with the first 320 springtail contacting the knuckle hub 302 and the second springtail 322 contacting the split yoke assembly 330. The maximum relative bent position between the knuckle hub 302 and the yoke assembly 330 is reached when the ramped hub surface 308 contacts the ramped yoke surface 344, compressing the torsion spring 318 (se FIG. 17). When manual bending pressure on the knuckle assembly 300 is released, the torsion spring 318 biases the knuckle assembly 300 into the straight position of FIG. 18, where the yoke flat stop-surface 346 abuts against the hub flat stop surface 310.

A camera-mounting collar 350 is coupled to a downstream end of the split yoke assembly 330 of the knuckle assembly 300. As shown in FIGS. 15-18, the camera housing 48 is coupled to the camera-mounting collar 350 of the knuckle assembly 300 by a camera housing mounting screw 348. The camera-mounting collar 350 includes an aperture 354 that is in communication with the central through bore 342 of the split yoke assembly 330 and the central through bore 306 of the knuckle hub 302, which constitute a cable passageway for passage of cables between the camera housing 48 and controller box 34 of FIG. 1. In alternative embodiments, not shown, the camera-mounting collar is coupled to the knuckle hub of the knuckle assembly and the split yoke assembly is coupled to the telescoping extension tubes.

Although various embodiments that incorporate the invention have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted", "connected", "supported", and "coupled", and variations thereof are used broadly and encompass direct and indirect mountings, connections, supports, and couplings. Further, "connected" and "coupled" are not restricted to physical, mechanical, or electrical connections or couplings.

What is claimed is:

1. A system for internal inspection of a power generation machine, comprising:
   a single-axis, extendable inspection scope, for insertion into an inspection port of a power generation machine, having:
   first, and second nested, telescoping tubes, respectively having proximal and distal ends, inner and outer circumferential surfaces, and axial length,
   the second telescoping tube having a coaxially oriented linear track on its inner or outer circumferential surface,
   the first telescoping tube having a first anti-rotation collar coupled proximal the distal end thereof, which defines a groove that is in sliding engagement with the linear track of the second telescoping tube;
   first and second nested drive tubes retained within the telescoping tubes, respectively having proximal and distal ends and axial length,
   the first drive tube having a first drive bushing coupled to the distal end thereof, both of which are rotatable within the telescoping tubes, the first drive bushing defining a bore with female drive threads,
   the second drive tube defining external male drive threads in engagement with the first drive bushing female threads;
   a camera-mounting collar rigidly coupled to the respective distal ends of a circumscribing one of the first or the second telescoping tubes and the second drive tube, preventing relative rotation thereof;
   a rotatable drive hub coupled to the proximal end of the first drive tube, for selective rotation thereof;
   a mounting flange coupled to the circumscribing one of the first or the second telescoping tubes, for affixation to a power generation machine inspection port; and
   a spherical camera, having a 360 degree field of view, coupled to the camera mounting collar, for insertion into a power generation machine and capture of inspection images therein.

2. The system of claim 1, further comprising:
   the first telescoping tube circumscribing the second telescoping tube, said first anti-rotation collar circumscribed by and in contact with the inner circumferential surface of the first telescoping tube; and
   the linear track coupled to the outer circumferential surface of the second telescoping tube.

3. The system of claim 1, further comprising:
   a distal portion of the rotatable drive hub oriented within the proximal end of the circumscribing first or second telescoping tube, and engaged within the first drive tube;
   a proximal portion of the drive hub coupled to a driven gear that is external the first telescoping tube;
   a first drive gear engaged with the driven gear, for rotating the driven gear and the drive hub; and
   a drive apparatus coupled to the first drive gear.

4. The system of claim 3, the drive apparatus comprising a hand crank.

5. The system of claim 3, the drive apparatus comprising an electric motor.

6. The system of claim 3, further comprising:
   the first drive gear directly engaged with the driven gear, driven by a hand crank drive apparatus; and
   a second drive gear directly engaged with the driven gear, driven by an electric motor; the respective drive gears independently and selectively capable of driving the driven gear.

7. The system of claim 2, further comprising an intermediate telescoping tube interposed and nested between the first and second telescoping tubes, the intermediate telescoping tube defining a coaxially oriented, intermediate linear track on an outer circumferential surface thereof, for engagement with the anti-rotation collar of the first telescoping tube, and an anti-rotation collar coupled proximal a distal end thereof, in sliding engagement with the axial track of the second telescoping tube.

8. The system of claim 1, further comprising at least one additional drive tube interposed and nested between the first and second drive tubes, each additional drive tube defining male drive threads on an outer circumferential surface thereof, for engagement with female threads of a drive bushing of a circumscribing drive tube, and a drive bushing coupled proximal a distal end thereof, in engagement with drive threads of an inscribed drive tube retained therein.

9. The system of claim 1, further comprising a camera housing coupled to the camera collar, enveloping the camera.

10. The system of claim 9, the camera housing further comprising an illumination system, coupled thereto, for illuminating the camera field of view.

11. The system of claim 1, further comprising:
    a position encoder, for correlating hub rotation with axial displacement of the camera field of view; and
    an image processing system coupled to the camera and the position encoder, for storing plural images taken at different camera axial displacement positions, and for combining plural inspection images into a composite image.

12. A system for internal inspection of a power generation machine, comprising:
    a single-axis, extendable inspection scope, which defines an extension axis, for insertion into an inspection port of a power generation machine, the scope having:
    first, second, third, and fourth nested, telescoping tubes, respectively having proximal and distal ends and axial length, the second, third and fourth telescoping tubes respectively having a coaxially oriented linear track on an outer circumferential surface thereof,
the first telescoping tube having a first anti-rotation collar coupled proximal the distal end thereof, in sliding engagement with the linear track of the second telescoping tube,
the second telescoping tube having a second anti-rotation collar coupled proximal the distal end thereof, in sliding engagement with the linear track of the third telescoping tube,
the third telescoping tube having a third anti-rotation collar coupled proximal the distal end thereof, in sliding engagement with the linear track of the fourth telescoping tube;
first, second and third nested drive tubes retained within the telescoping tubes, respectively having proximal and distal ends and axial length,
the first drive tube having a first drive bushing coupled to the distal end thereof, both of which are rotatable within the fourth telescoping tube, the first drive bushing defining a bore with female drive threads,
the second drive tube defining external male threads in engagement with the first drive bushing female threads, and having a second drive bushing coupled to the distal end thereof, both of which are rotatable within the fourth telescoping tube, the second drive bushing defining a bore with female drive threads,
the third drive tube defining external male threads in engagement with the second drive bushing female threads;
a camera-mounting collar rigidly coupled to the respective distal ends of the fourth telescoping tube and the third drive tube, preventing relative rotation thereof;
a rotatable drive hub coupled to the proximal end of the first drive tube, for selective rotation thereof;
a mounting flange coupled to the first telescoping tube, for affixation to a power generation machine inspection port; and
a spherical camera, having a 360 degree field of view, coupled to the camera mounting collar, for insertion into a power generation machine and capture of inspection images therein.

13. The system of claim 12, at least one of the anti-rotation collars retaining a ball bearing that is in engagement within the axial groove of the second telescoping tube.

14. The system of claim 12, further comprising:
a distal portion of the rotatable drive hub oriented within the proximal end of the first telescoping tube, and engaged within the first drive tube;
a proximal portion of the drive hub coupled to a driven gear that is external the first telescoping tube;
a first drive gear engaged with the driven gear, for rotating the driven gear and the drive hub; and
a drive apparatus coupled to the first drive gear.

15. The system of claim 14, further comprising:
a controller box retaining the driven gear and the first drive gear, the first drive gear directly engaged with the driven gear, driven by a hand crank drive apparatus; and
a second drive gear directly engaged with the driven gear, driven by an electric motor, both of which are retained within the drive gear housing;
the respective drive gears independently and selectively capable of driving the driven gear; and a visual display incorporated within the controller box, for viewing images captured within the camera field of view.

16. The system of claim 12, further comprising a camera housing coupled to the camera collar, enveloping the camera; and an illumination system, coupled to the camera housing, for illuminating the camera field of view.

17. The system of claim 12, further comprising:
a position encoder, for correlating hub rotation with axial displacement of the camera field of view; and
an image processing system coupled to the camera and the position encoder, for storing plural images taken at different camera axial displacement positions, and for combining plural inspection images into a navigable composite image.

18. A method for internal inspection of a power generation machine, comprising:
providing a system for inspection of a power generation machine, the system including:
a single-axis, extendable inspection scope, for insertion into an inspection port of a power generation machine, having:
first, and second nested, telescoping tubes, respectively having proximal and distal ends, inner and outer circumferential surfaces, and axial length,
the second telescoping tube having a coaxially oriented linear track on its inner or outer circumferential surface,
the first telescoping tube having a first anti-rotation collar coupled proximal the distal end thereof, which defines a groove that is in sliding engagement with the linear track of the second telescoping tube;
first and second nested drive tubes retained within the telescoping tubes, respectively having proximal and distal ends and axial length,
the first drive tube having a first drive bushing coupled to the distal end thereof, both of which are rotatable within the telescoping tubes, the first drive bushing defining a bore with female drive threads,
the second drive tube defining external male drive threads in engagement with the first drive bushing female threads;
a camera-mounting collar rigidly coupled to the respective distal ends of a circumscribing one of the first or the second telescoping tubes and the second drive tube, preventing relative rotation thereof;
a rotatable drive hub coupled to the proximal end of the first drive tube, for selective rotation thereof;
a mounting flange coupled to the circumscribing one of the first or the second telescoping tubes, for affixation to a power generation machine inspection port; and
a spherical camera, having a 360 degree field of view, coupled to the camera mounting collar, for insertion into a power generation machine and capture of inspection images therein;
affixing the mounting flange to an inspection port, or other machine-inspection entry site in a power generation machine, while inserting the inspection scope therein;
rotating the drive hub, thereby rotating the first drive tube, and advancing the second drive tube and the camera field of view within the power generation machine, without rotating the camera about the inspection scope extension axis; and
capturing respective camera images within the power generation machine at plural positions, as the camera field of view is advanced within the machine.

19. The method of claim 18, further comprising:
  the provided system for inspection further including a position encoder, for correlating hub rotation with axial displacement of the camera field of view, the position encoder generating position output data, and an image processing system coupled to the camera and the position encoder, for storing plural images taken at different camera axial displacement positions, and for combining plural inspection images into a composite image;
  the image processing system determining axial displacement position of the camera field of view with the position encoder output data, correlating the determined axial displacement position with a corresponding position within the camera image; and
  the image processing system combining plural inspection images into a navigable composite image.

20. The method of claim 19, the provided system for inspection further including:
  the first telescoping tube circumscribing the second telescoping tube, said first anti-rotation collar circumscribed by and in contact with the inner circumferential surface of the first telescoping tube; and
  the linear track coupled to the outer circumferential surface of the second telescoping tube.

* * * * *